United States Patent [19]

Römer et al.

[11] Patent Number: 4,544,771

[45] Date of Patent: Oct. 1, 1985

[54] HALOGENOBIPHENYL DERIVATIVES

[75] Inventors: Michael Römer, Rodgau; Joachim Krause, Dieburg; Georg Weber, Erzhausen, all of Fed. Rep. of Germany

[73] Assignee: Merck Patent Gesellschaft mit beschränkter Haftung, Darmstadt, Fed. Rep. of Germany

[21] Appl. No.: 699,898

[22] Filed: Feb. 8, 1985

Related U.S. Application Data

[62] Division of Ser. No. 472,307, Mar. 4, 1983, Pat. No. 4,505,838.

[30] Foreign Application Priority Data

Mar. 6, 1982 [DE] Fed. Rep. of Germany ....... 3208089

[51] Int. Cl.$^4$ ..................... C07C 49/813; C07C 69/76
[52] U.S. Cl. ................................. 568/329; 568/331; 560/51; 560/53
[58] Field of Search ................. 560/51, 53; 568/329, 568/331

[56] References Cited

U.S. PATENT DOCUMENTS

| | | | |
|---|---|---|---|
| 4,065,489 | 12/1977 | Steinstrasser et al. | 252/299.65 |
| 4,229,215 | 11/1981 | Krause et al. | 252/299.63 |
| 4,368,135 | 1/1983 | Osman | 252/299.63 |
| 4,382,012 | 5/1983 | Eidenschink et al. | 252/299.63 |
| 4,410,445 | 10/1983 | Baur et al. | 252/299.63 |
| 4,415,470 | 11/1983 | Eidenschink et al. | 252/299.63 |
| 4,419,264 | 12/1983 | Eidenschink et al. | 252/299.63 |

FOREIGN PATENT DOCUMENTS

| | | | |
|---|---|---|---|
| 0019665 | 12/1980 | European Pat. Off. | 252/299.65 |
| 2939782 | of 0000 | Fed. Rep. of Germany | 252/299.64 |
| 2933563 | 2/1981 | Fed. Rep. of Germany | 252/299.63 |
| 55-47642 | 4/1980 | Japan | 252/299.64 |
| 55-81849 | 6/1980 | Japan | 252/299.65 |
| 57-9742 | 1/1982 | Japan | 252/299.73 |

OTHER PUBLICATIONS

Demus et al., Flussige Kristalle in Tabellen, pp. 186–190, 192–195, (1974).

Grey, Molecular Structure & the Properties of Liquid Crystals, pp. 224–225, 246, Academic Press, N.Y., (1962).

Gray et al., J. Chem. Soc., 1959, pp. 1545–1550.

*Primary Examiner*—James H. Reamer
*Attorney, Agent, or Firm*—Millen & White

[57] ABSTRACT

Halogenobiphenyl derivatives of Formula I

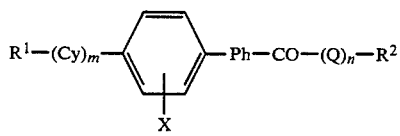

wherein $R^1$ and $R^2$ are each alkyl or alkoxy in each case of 1–10 C atoms, Cy is 1,4-cyclohexylene, Ph is 1,4-phenylene, Q is —O—Cy— or —O—Ph—, m and n are each 0 or 1 and X is F, Cl or Br, can be used as components of liquid crystal dielectrics for electrooptical display elements.

14 Claims, No Drawings

HALOGENOBIPHENYL DERIVATIVES

This is a division of application Ser. No. 472,307 filed Mar. 4, 1983, now U.S. Pat. No. 4,505,538.

The present invention relates to new halogenobiphenyl derivatives having liquid crystalline properties.

SUMMARY OF THE INVENTION

It is an object of this invention to provide new liquid crystal compounds which are suitable as components of liquid crystal dielectrics, in particular for nematic phases with a high optical anisotropy.

Upon further study of the specification and appended claims, further objects and advantages of this invention will become apparent to those skilled in the art.

These objects have been achieved by providing halogenobiphenyl compounds of Formula I

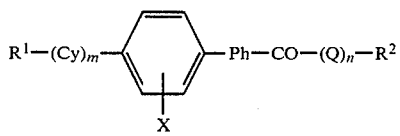

I wherein $R^1$ and $R^1$ are each alkyl or alkoxy each of 1-10 C atoms, Cy is 1,4-cyclohexylene, Ph is 1,4-phenylene, Q is —O—Cy— or —O—Ph—, m and n are each 0 or 1 and X is F, Cl or Br.

This invention also relates to the use of the compounds of Formula I as components of liquid crystal dielectrics, liquid crystal dielectrics containing at least one compound of Formula I, and electrooptical display elements which contain such dielectrics.

DETAILED DISCUSSION

Like similar compounds, for example those known from German Offenlegungsschrift No. 2,800,553, these substances can be used as components of liquid crystal dielectrics, in particular for displays which are based on the principle of the twisted cell.

It has been found that the compounds of Formula I are outstandingly suitable as components of liquid crystal dielectrics. In particular, liquid crystal phases with a wide nematic range, a relatively high optical anisotropy and a positive dielectric anisotropy can be prepared using these compounds.

The compounds of Formula I are colorless in the pure state, and form liquid crystal mesophases in a temperature range which is advantageous for electrooptical use.

Those compounds of Formula I which are optically active are suitable as chiral doping substances for the production of cholesteric phases such as can also be used for White-Taylor dyestuff cells. In low concentrations, these chiral compounds are capable of preventing interference with the optical phenomena in the twisted cell by "reverse twist" (compare Mol. Cryst. Liq. Cryst., Volume 34 (Letters), pages 211-217 [1977]).

This invention thus relates to compounds of Formula I, and to a process for their preparation, comprising diazotizing an aminobiphenyl derivative of the Formula II

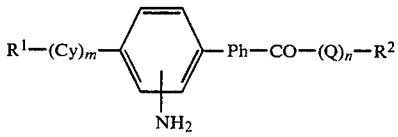

II wherein
$R^1$, $R^2$, Cy, Ph, Q, m and n are as defined for Formula I, and replacing the diazonium group by an X atom by known methods;

or, for the preparation of a compound of Formula I wherein $R^2$ is alkyl and n is 0, reacting a halogenobiphenyl derivative of Formula III

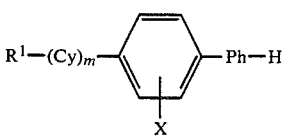

III wherein $R^1$, Cy, Ph, m and X are as defined for Formula I, with a carboxylic acid of Formula IV

 IV wherein $R^3$ is alkyl of 1-10 C atoms, or with one of its reactive derivatives, in the presence of an acid or a Lewis acid; or for the preparation of a compound of the Formula I wherein $R^2$ is alkoxy and/or n is 1, reacting a carboxylic acid of Formula V

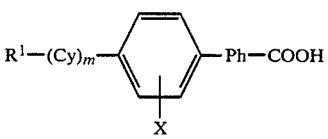

V wherein $R^1$, Cy, Ph, m and X are as defined for Formula I, or one of its reactive derivatives, with a hydroxy compound of Formula VI

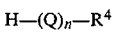 VI wherein $R^4$ is alkoxy of 1-10 C atoms, or, when n is 1, also alkyl of 1-10 C atoms, and Q and n are as defined for Formula I, or one of its reactive derivatives.

In the preceding and following text, $R^1$, $R^2$, Cy, Ph, Q, m, n, X, $R^3$ and $R^4$ have the meaning given, unless expressly indicated otherwise.

The compounds of Formula I include ketones of Formula Ia and esters of Formula Ib:

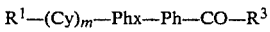 Ia

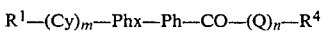 Ib wherein Phx is 1,4-phenylene radical substituted by an X atom.

Specifically, Formula I includes ketones of Formulae Ic and Id and esters of Formulae Ie to Ij:

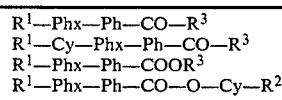

| | |
|---|---|
| R¹—Phx—Ph—CO—O—Ph—R² | Ig |
| R¹—Cy—Phx—Ph—COOR³ | Ih |
| R¹—Cy—Phx—Ph—CO—O—Cy—R² | Ii |
| R¹—Cy—Phx—Ph—CO—O—Ph—R² | Ij | wherein the alkyl and alkoxy groups in each case contain 1-10, preferably 1-6 and in particular 3, 4, 5 or 6 C atoms.

The compounds of Formulae Id and Ie are preferred.

The radicals R¹ and R² are preferably alkyl.

In the compounds of Formulae I and Ia, Ib, Id, If, Ih, Ii and Ij, those stereoisomers wherein the two substituents on the cyclohexylene radicals are in each case in the trans-position relative to one another are preferred.

In the compounds of Formulae I and Ia to Ij, the alkyl and alkoxy groups are preferably straight-chained. Alkyl is preferably methyl, ethyl, n-propyl, n-butyl, n-pentyl or n-hexyl, and furthermore preferably n-heptyl, n-octyl, n-nonyl or n-decyl; and alkoxy is preferably methoxy, ethoxy, n-propoxy, n-butoxy, n-pentyloxy or n-hexyloxy, and furthermore preferably n-heptyloxy, n-octyloxy, n-nonyloxy or n-decyloxy.

Compounds of Formula I and Ia to Ij with branched alkyl or alkoxy groups may occasionally be of importance because of their better solubility in the customary liquid crystal base materials, but especially as chiral doping substances, if they are optically active. Branched groups of this type as a rule contain not more than one chain branching. Preferred branched alkyl radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-heptyl (=1-methylhexyl), or 2-octyl (=1-methylheptyl); and preferred branched alkoxy radicals are isopropoxy, 2-methylpropoxy, 2-methylbutoxy, 3-methylbutoxy, 2-methylpentyloxy, 3-methylpentyloxy, 2-ethylhexyloxy, 1-methylhexyloxy and 1-methylheptyloxy.

The compounds of Formula I are otherwise prepared by methods which are known per se, such as are described in the literature (for example in the standard works, such as Houben-Weyl, Methoden der Organischen Chemie [Methods of Organic Chemistry], Georg-Thieme-Verlag, Stuttgart), and in particular under reaction conditions which are known and suitable for the reactions mentioned. It is also possible to utilize variants which are known per se and are not mentioned here in more detail.

If desired, the starting substances can also be formed in situ, in a manner such that they are not isolated from the reaction mixture but are immediately reacted further to give the compounds of Formula I.

The halogenobiphenyl derivatives of Formula I can be prepared from the amines of Formula II by the methods of the Schiemann reaction (compare, for example, The Merck Index, 9th Edition, Merck & Co., Inc., Rahway, N.J., U.S.A., 1976, page ONR-80) or the Sandmeyer reaction (compare, for example, The Merck Index, Loc. cit., page ONR-79).

Advantageously, the diazotization is first carried out with a salt or ester of nitrous acid (such as $NaNO_2$ or butyl nitrite) in an aqueous acidic phase, it being possible to use as the acid, for example, HF, HCl, HBr, $H_2SO_4$ or $HBF_4$, at temperatures of about −20° to +10°. An additional inert solvent may be present, for example an ether, such as tetrahydrofuran or dioxane, or a hydrocarbon, such as toluene or xylene.

To prepare the chlorine compounds (I, X is F), the diazotization is advantageously carried out in $HBF_4$. The diazonium tetrafluoborates are thereby formed, and can be decomposed at temperatures of only about 10° to 100°. If the diazotization is carried out with $NaNO_2$ in anhydrous HF, the desired fluorine compound is obtained directly by subsequent warming.

The diazonium group is preferably replaced by Cl or Br in aqueous solution in the presence of $Cu_2Cl_2$ or $Cu_2Br_2$ at temperatures of 30° to 100°.

The ketones of Formula Ia (=I, R² is alkyl, n is 0) can furthermore be obtained by acylation of the halogenobiphenyl derivatives of Formula III with carboxylic acids of Formula IV or their reactive derivatives, advantageously in the presence of an acid catalyst and an inert solvent at temperatures of about 0° to about 120°. Suitable derivatives of the carboxylic acids of Formula IV are, above all, their anhydrides and halides, for example the corresponding acid chlorides and acid bromides. Suitable catalysts include acids, such as HF, $H_3PO_4$ or polyphosphoric acid, or, preferably, Lewis acids, such as $AlCl_3$, $AlBr_3$, $SnCl_4$, $ZnCl_2$, $FeCl_3$, $SbCl_5$ or $BF_3$ or its etherate, and examples of suitable solvents include $CS_2$, hydrocarbons, such as hexane, nitrobenzene or tetramethylenesulfone.

The esters of Formula Ib can also be obtained by esterification of the carboxylic acids of Formula V with alcohols or phenols of Formula VI.

Particularly suitable reactive derivatives of these carboxylic acids are the acid halides, above all the chlorides and bromides, and furthermore the anhydrides, for example also mixed anhydrides of the formula $R^1$—(Cy)$_m$—Phx—Ph—CO—O—COCH$_3$, azides and esters, in particular alkyl esters of 1-4 C atoms in the alkyl group.

Suitable reactive derivatives of the alcohols or phenols of Formula VI include, in particular, the corresponding metal alcoholates or phenolates of the formula M—(Q)$_n$—R⁴, in which M is one equivalent of a metal, preferably in alkali metal, such as Na or K.

The esterification is advantageously carried out in the presence of an inert solvent. Particularly suitable solvents include ethers, such as diethyl ether, di-n-butyl ether, tetrahydrofuran, dioxane or anisole, ketones, such as acetone, butanone or cyclohexanone, amides, such as dimethylformamide or phosphoric acid hexamethyltriamide, hydrocarbons, such as benzene, toluene or xylene, halogenohydrocarbons, such as carbon tetrachloride or tetrachloroethylene, and sulfoxides, such as dimethylsulfoxide or sulfolane. Water-immiscible solvents may advantageously be used at the same time for azeotropic distillation of the water formed during the esterification. An excess of an organic base, for example pyridine, quinoline or triethylamine, may occasionally also be used as a solvent for the esterification. The esterification can also be carried out in the absence of a solvent, for example by simple heating of the components in the presence of sodium acetate.

The reaction temperature is usually −50° to +250°, preferably −20° to +80°. At these temperatures, the esterification reaction has as a rule ended after 15 minutes to 48 hours.

Specifically, the reaction conditions for the esterification largely depend on the nature of the starting substance used. Thus, a free carboxylic acid of Formula V is as a rule reacted with an alcohol or phenol of Formula VI in the presence of a strong acid, for example a mineral acid, such as hydrochloric acid or sulfuric acid.

A preferred procedure is the reaction of an acid anhydride or, in particular, an acid chloride with an alcohol, preferably in a basic medium, typical bases being alkali metal hydroxides, such as sodium or potassium hydroxide, alkali metal carbonates or bicarbonates, such as sodium carbonate, sodium bicarbonate, potassium carbonate or potassium bicarbonate, alkali metal acetates, such as sodium or potassium acetate, alkaline earth metal hydroxides, such as calcium hydroxide, or organic bases, such as triethylamine, pyridine, lutidine, collidine or quinoline.

Another preferred embodiment of the process according to this invention comprises first converting the hydroxy compound of Formula VI to be esterified into the sodium alcoholate or phenolate or potassium alcoholate or phenolate, for example by treatment with ethanolic sodium hydroxide solution or potassium hydroxide solution, isolating this alcoholate or phenolate, suspending it in acetone or diethyl ether, together with sodium bicarbonate or potassium carbonate, while stirring, and adding a solution of the acid chloride or anhydride in diethyl ether, acetone or dimethylformamide to this suspension, advantageously at temperatures of about $-25°$ to $+20°$.

Some of the starting substances of Formulae II to VI and their reactive derivatives are known, and all of them can be prepared analogously by the methods for known compounds, from substances which are known from the literature.

Thus, the amines of Formula II can be obtained, for example, by nitration of biphenyl derivatives (corresponding to Formula I, but X is H) and subsequent reduction, and the starting substances of Formulae III and V can be obtained analogously from the unsubstituted compounds (corresponding to Formulae III and V, but X is H), by nitration, reduction to give the amino compound, diazotization and a Schiemann or Sandmeyer reaction.

The dielectrics according to this invention comprise 2 to 15, preferably 3 to 12, components, at least one of which is a compound of Formula I. The other constituents are preferably selected from the nematic or nematogenic substances, in particular the known substances, from the classes of azoxybenzenes, benzylideneanilines, biphenyls, terphenyls, phenyl- or cyclohexyl-benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexyl-pyrimidines, phenyl- or cyclohexyl-dioxanes, optionally halogenated stilbenes, benzyl phenyl ethers, tolanes and substituted cinnamic acids. The most important compounds which can be used as constituents of such liquid crystal dielectrics can be characterized by Formula VII

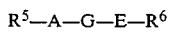

$$R^5—A—G—E—R^6 \quad \text{VII}$$

wherein A and E are each a carbocyclic or heterocyclic ring system from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline; G is —CH=CH—, —CH=CL—, —CH≡C—, —CO—O—, —CO—S—, —CH=N—, —N(O)=N—, —CH=N(O)—, CH₂— CH₂—, —CH₂—O—, —CH₂—S—, —COO—Ph—COO— or a C—C single bond; L is halogen, preferably chlorine, or CN; and $R^5$ and $R^6$ are alkyl, alkoxy, alkanoyloxy or alkoxycarbonyloxy with up to 18, preferably up to 8, carbon atoms, or one of these radicals is also CN, NC, NO₂, CF₃, F, Cl or Br. In most of these compounds, $R^5$ and $R^6$ differ, one of these radicals usually being an alkyl or alkoxy group. Many such substances or mixtures thereof are commercially available.

The dielectrics according to this invention contain about 0.1 to 30%, preferably 2 to 25%, of one or more compounds of Formula I.

The dielectrics according to this invention are prepared in a manner which is customary per se. As a rule, the components are dissolved in one another, advantageously at elevated temperature. If a temperature above the clear point of the main constituent is chosen, the completeness of the solution operation can be particularly easily observed.

The liquid crystal dielectrics according to this invention can be modified by suitable additives such that they can be used in all the types of liquid crystal display elements which have hitherto been disclosed.

Such additives are familiar to the expert and are described in detail in the literature. For example, dichroic dyestuffs or substances for modifying the dielectric anisotropy, the viscosity, the conductivity and/or the orientation of the nematic phases can be added. Such substances are described, for example, in German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the melting point and c.p. is the clear point of a liquid crystal substance.

EXAMPLE 1

180 ml of 35% aqueous tetrafluoboric acid solution is added dropwise to a suspension of 36.7 g of 4'-acetyl-2-amino-4-(trans-4-pentylcyclohexyl)-biphenyl (m.p. 118°–123°; obtainable by nitration of 4'-acetyl-4-(trans-4-pentylcyclohexyl)-biphenyl and subsequent hydrogenation of the resulting crude 2-nitro compound over Raney nickel in tetrahydrofuran) in 180 ml of dioxane at 15°–20°, while stirring, and a solution of 7.2 g of NaNO₂ in 25 ml of water is then added dropwise at 0°. The mixture is subsequently stirred for 6 hours, the temperature being allowed to rise to 15°. After customary working up (extraction with toluene, filtration over silica gel), 4'-acetyl-2-fluoro-4-(trans-4-pentylcyclohexyl)-biphenyl of m.p. 81° and c.p. 170° is obtained.

EXAMPLES 2 TO 49

The following compounds are obtained analogously to Example 1 from the corresponding amino compounds:

2. 4'-Acetyl-2-fluoro-4-methylbiphenyl.

3. 4'-Acetyl-2-fluoro-4-ethylbiphenyl.
4. 4'-Acetyl-2-fluoro-4-propylbiphenyl.
5. 4'-Acetyl-2-fluoro-4-butylbiphenyl.
6. 4'-Acetyl-2-fluoro-4-pentylbiphenyl.
7. 4'-Acetyl-2-fluoro-4-hexylbiphenyl.
8. 4'-Acetyl-2-fluoro-4-heptylbiphenyl.
9. 4'-Acetyl-2-fluoro-4-octylbiphenyl.
10. 4'-Acetyl-2-fluoro-4-nonylbiphenyl.
11. 4'-Acetyl-2-fluoro-4-decylbiphenyl.
12. 4'-Acetyl-2-fluoro-4-methoxybiphenyl.
13. 4'-Acetyl-2-fluoro-4-ethoxybiphenyl.
14. 4'-Acetyl-2-fluoro-4-propoxybiphenyl.
15. 4'-Acetyl-2-fluoro-4-butoxybiphenyl.
16. 4'-Acetyl-2-fluoro-4-pentyloxybiphenyl.
17. 4'-Acetyl-2-fluoro-4-hexyloxybiphenyl.
18. 4'-Acetyl-2-fluoro-4-heptyloxybiphenyl.
19. 4'-Acetyl-2-fluoro-4-octyloxybiphenyl.
20. 4'-Acetyl-2-fluoro-4-nonyloxybiphenyl.
21. 4'-Acetyl-2-fluoro-4-decyloxybiphenyl.
22. 4'-Acetyl-2-fluoro-4-(trans-4-methylcyclohexyl)-biphenyl.
23. 4'-Acetyl-2-fluoro-4-(trans-4-ethylcyclohexyl)-biphenyl.
24. 4'-Acetyl-2-fluoro-4-(trans-4-propylcyclohexyl)-biphenyl.
25. 4'-Acetyl-2-fluoro-4-(trans-4-butylcyclohexyl)-biphenyl.
26. 4'-Acetyl-2-fluoro-4-(trans-4-hexylcyclohexyl)-biphenyl.
27. 4'-Acetyl-2-fluoro-4-(trans-4-heptylcyclohexyl)-biphenyl.
28. 4'-Acetyl-2-fluoro-4-(trans-4-octylcyclohexyl)-biphenyl.
29. 4'-Acetyl-2-fluoro-4-(trans-4-nonylcyclohexyl)-biphenyl.
30. 4'-Acetyl-2-fluoro-4-(trans-4-decylcyclohexyl)-biphenyl.
31. 4'-Acetyl-2-fluoro-4-(trans-4-methoxycyclohexyl)-biphenyl.
32. 4'-Acetyl-2-fluoro-4-(trans-4-ethoxycyclohexyl)-biphenyl.
33. 4'-Acetyl-2-fluoro-4-(trans-4-propoxycyclohexyl)-biphenyl.
34. 4'-Acetyl-2-fluoro-4-(trans-4-butoxycyclohexyl)-biphenyl.
35. 4'-Acetyl-2-fluoro-4-(trans-4-pentyloxycyclohexyl)-biphenyl.
36. 4'-Acetyl-2-fluoro-4-(trans-4-hexyloxycyclohexyl)-biphenyl.
37. 4'-Acetyl-2-fluoro-4-(trans-4-heptyloxycyclohexyl)-biphenyl.
38. 4'-Acetyl-2-fluoro-4-(trans-4-octyloxycyclohexyl)-biphenyl.
39. 4'-Acetyl-2-fluoro-4-(trans-4-nonyloxycyclohexyl)-biphenyl.
40. 4'-Acetyl-2-fluoro-4-(trans-4-decyloxycyclohexyl)-biphenyl.
41. 2-Fluoro-4'-propionyl-4-propylbiphenyl.
42. 2-Fluoro-4'-propionyl-4-butylbiphenyl.
43. 2-Fluoro-4'-propionyl-4-pentylbiphenyl.
44. 2-Fluoro-4'-propionyl-4-methoxybiphenyl.
45. 2-Fluoro-4'-propionyl-(trans-4-propylcyclohexyl)-biphenyl.
46. 2-Fluoro-4'-propionyl-(trans-4-pentylcyclohexyl)-biphenyl.
47. 4'-Butyryl-2-fluoro-4-(trans-4-propylcyclohexyl)-biphenyl.
48. 4'-Decanoyl-2-fluoro-4-(trans-4-pentylcyclohexyl)-biphenyl.
49. 4'-Acetyl-3-fluoro-4-(trans-4-pentylcyclohexyl)-biphenyl.

EXAMPLE 50

A solution of 7.2 g of $NaNO_2$ in 25 ml of water is added to a suspension of 36.7 g of 4'-acetyl-2-amino-4-(trans-4-pentylcyclohexyl)-biphenyl in 150 ml of 15% aqueous hydrochloric acid at −5° in the course of 0.5 hours. The solution thus obtained is added dropwise, at 0°–5° in the course of 1 hour, to a Cu(I) salt solution which has been prepared from 25 g of $CuSO_4.5H_2O$, 8.8 g of NaCl, 6.3 g of $Na_2SO_3$, 100 ml of water and 40 ml of 32% hydrochloric acid. After the mixture has been heated to 40° for half an hour, it is cooled and extracted with $CH_2Cl_2$ and the product is worked up in the customary manner. 4'-Acetyl-2-chloro-4-(trans-4-pentylcyclohexyl)-biphenyl is obtained.

EXAMPLES 51 TO 55

The following compounds are obtained analogously to Example 50 from the corresponding amino compounds:
51. 2-Chloro-4'-acetyl-4-propylbiphenyl.
52. 2-Chloro-4'-acetyl-4-butylbiphenyl.
53. 2-Chloro-4'-acetyl-4-pentylbiphenyl.
54. 2-Chloro-4'-acetyl-4-(trans-4-propylcyclohexyl)-biphenyl.
55. 2-Chloro-4'-acetyl-4-(trans-4-pentylcyclohexyl)-biphenyl.

EXAMPLE 56

The procedure followed is analogous to Example 50, but HBr is used instead of HCl and NaBr is used instead of NaCl, and 4'-acetyl-2-bromo-4-(trans-5-pentylcyclohexyl)-biphenyl is obtained.

EXAMPLE 57

27 g of $AlCl_3$ is added to a mixture of 32.4 g of 2-fluoro-4-(trans-4-pentylcyclohexyl)-biphenyl and 200 ml of $CS_2$ at 20°, while stirring; 10 g of acetic anhydride is then added dropwise, while stirring and boiling, and the mixture is boiled for another hour. The mixture is cooled, filtered and decomposed by being discharged into hydrochloric acid/ice, and 4'-acetyl-2-fluoro-4-(trans-4-pentylcyclohexyl)-biphenyl of m.p. 81° and c.p. 170° is obtained.

The compounds mentioned in Examples 2 to 56 can be obtained analogously.

EXAMPLE 58

28.6 g of 2'-fluoro-4'-pentylbiphenyl-4-carboxylic acid (obtainable by nitration of 4'-pentylbiphenyl-4-carboxylic acid to give the 2'-nitro derivative, reduction to give the 2'-amino compound and a Schiemann reaction) is boiled with 24 g of $SOCl_2$ for one hour, the mixture is evaporated, the resulting crude acid chloride is dissolved in 150 ml of toluene, 7.9 g of pyridine and 6 g of propanol are added and the mixture is boiled for 2 hours. The mixture is cooled and washed with water and the organic phase is dried over $Na_2SO_4$ and evaporated. Propyl 2'-fluoro-4'-pentylbiphenyl-4-carboxylate is obtained. Analogously, there are obtained:
59. Methyl 2'-fluoro-4'-propylbiphenyl-4-carboxylate.
60. Ethyl 2'-fluoro-4'-propylbiphenyl-4-carboxylate.
61. Propyl 2'-fluoro-4'-propylbiphenyl-4-carboxylate.
62. Butyl 2'-fluoro-4'-propylbiphenyl-4-carboxylate.

63. Pentyl 2'-fluoro-4'-propylbiphenyl-4-carboxylate.
64. Hexyl 2'-fluoro-4'-propylbiphenyl-4-carboxylate.
65. Heptyl 2'-fluoro-4'-propylbiphenyl-4-carboxylate.
66. Octyl 2'-fluoro-4'-propylbiphenyl-4-carboxylate.
67. 1-Methylheptyl 2'-fluoro-4'-propylbiphenyl-4-carboxylate.
68. Nonyl 2'-fluoro-4'-propylbiphenyl-4-carboxylate.
69. Decyl 2'-fluoro-4'-propylbiphenyl-4-carboxylate.
70. Trans-4-propylcyclohexyl 2'-fluoro-4'-propylbiphenyl-4-carboxylate.
71. Trans-4-butylcyclohexyl 2'-fluoro-4'-propyl-biphenyl-4-carboxylate.
72. Trans-4-pentylcyclohexyl 2'-fluoro-4'-propyl-biphenyl-4-carboxylate.
73. p-Propylphenyl 2'-fluoro-4'-propylbiphenyl-4-carboxylate.
74. p-Butylphenyl 2'-fluoro-4'-propylbiphenyl-4-carboxylate.
75. p-Pentylphenyl 2'-fluoro-4'-propylbiphenyl-4-carboxylate.
76. p-Methoxyphenyl 2'-fluoro-4'-propylbiphenyl-4-carboxylate.
77. p-Ethoxyphenyl 2'-fluoro-4'-propylbiphenyl-4-carboxylate.
78. Ethyl 4'-butyl-2'-fluorobiphenyl-4-carboxylate.
79. Propyl 4'-butyl-2'-fluorobiphenyl-4-carboxylate.
80. Butyl 4'-butyl-2'-fluorobiphenyl-4-carboxylate.
81. Pentyl 4'-butyl-2'-fluorobiphenyl-4-carboxylate.
72. Hexyl 4'-butyl-2'-fluorobiphenyl-4-carboxylate.
83. 1-Methylheptyl 4'-butyl-2'-fluorobiphenyl-4-carboxylate.
84. Trans-4-propylcyclohexyl 4'-butyl-2'-fluorobiphenyl-4-carboxylate.
85. Trans-4-pentylcyclohexyl 4'-butyl-2'-fluorophenyl-4-carboxylate.
86. p-Propylphenyl 4'-butyl-2'-fluorobiphenyl-4-carboxylate.
87. p-Pentylphenyl 4'-butyl-2'-fluorobiphenyl-4-carboxylate.
88. p-Methoxyphenyl 4'-butyl-2'-fluorobiphenyl-4-carboxylate.
89. p-Ethoxyphenyl 4'-butyl-2'-fluorobiphenyl-4-carboxylate.
90. Ethyl 2'-fluoro-4'-pentylbiphenyl-4-carboxylate.
91. Butyl 2'-fluoro-4'-pentylbiphenyl-4-carboxylate.
92. Pentyl 2'-fluoro-4'-pentylbiphenyl-4-carboxylate.
93. Hexyl 2'-fluoro-4'-pentylbiphenyl-4-carboxylate.
94. 1-Methylheptyl 2'-fluoro-4'-pentylbiphenyl-4-carboxylate.
95. Trans-4-propylcyclohexyl 2'-fluoro-4'-pentylbiphenyl-4-carboxylate.
96. Trans-4-pentylcyclohexyl 2'-fluoro-4'-pentylbiphenyl-4-carboxylate.
97. p-Propylphenyl 2'-fluoro-4'-pentylbiphenyl-4-carboxylate.
98. p-Pentylphenyl 2'-fluoro-4'-pentylbiphenyl-4-carboxylate.
99. p-Methoxyphenyl 2'-fluoro-4'-pentylbiphenyl-4-carboxylate.
100. p-Ethoxyphenyl 2'-fluoro-4'-pentylbiphenyl-4-carboxylate.
101. Ethyl 2'-fluoro-4'-(trans-4-propylcyclohexyl)-biphenyl-4-carboxylate.
102. Propyl 2'-fluoro-4'-(trans-4-propylcyclohexyl)-biphenyl-4-carboxylate.
103. Butyl 2'-fluoro-4'-(trans-4-propylcyclohexyl)-biphenyl-4-carboxylate.
104. Pentyl 2'-fluoro-4'-(trans-4-propylcyclohexyl)-biphenyl-4-carboxylate.
105. Hexyl 2'-fluoro-4'-(trans-4-propylcyclohexyl)-biphenyl-4-carboxylate.
106. 1-Methylheptyl 2'-fluoro-4'-(trans-4-propylcyclohexyl)-biphenyl-4-carboxylate.
107. Trans-4-propylcyclohexyl 2'-fluoro-4'-(trans-4-propyl-cyclohexyl)-biphenyl-4-carboxylate.
108. Trans-4-pentylcyclohexyl 2'-fluoro-4'-(trans-4-propylcyclohexyl)-biphenyl-4-carboxylate.
109. p-Propylphenyl 2'-fluoro-4'-(trans-4-propylcyclohexyl)-biphenyl-4-carboxylate.
110. p-Pentylphenyl 2'-fluoro-4'-(trans-4-propylcyclohexyl)-biphenyl-4-carboxylate.
111. p-Methoxyphenyl 2'-fluoro-4'-(trans-4-propylcyclohexyl)-biphenyl-4-carboxylate.
112. p-Ethoxyphenyl 2'-fluoro-4'-(trans-4-propylcyclohexyl)-biphenyl-4-carboxylate.
113. Ethyl 4'-(trans-4-butylcyclohexyl)-2'-fluorobiphenyl-4-carboxylate.
114. Propyl 4'-(trans-4-butylcyclohexyl)-2'-fluorobiphenyl-4-carboxylate.
115. Butyl 4'-(trans-4-butylcyclohexyl)-2'-fluorobiphenyl-4-carboxylate.
116. Pentyl 4'-(trans-4-butylcyclohexyl)-2'-fluorobiphenyl-4-carboxylate.
117. Hexyl 4'-(trans-4-butylcyclohexyl)-2'-fluorobiphenyl-4-carboxylate.
118. 1-Methylheptyl 4'-(trans-4-butylcyclohexyl)-2'-fluorobiphenyl-4-carboxylate.
119. Trans-4-propylcyclohexyl 4'-(trans-4-butylcyclohexyl)-2'-fluorobiphenyl-4-carboxylate.
120. Trans-4-pentylcyclohexyl 4'-(trans-4-butylcyclohexyl)-2'-fluorobiphenyl-4-carboxylate.
121. p-Propylphenyl 4'-(trans-4-butylcyclohexyl)-2'-fluorobiphenyl-4-carboxylate.
122. p-Pentylphenyl 4'-(trans-4-butylcyclohexyl)-2'-fluorobiphenyl-4-carboxylate.
123. p-Methoxyphenyl 4'-(trans-4-butylcyclohexyl)-2'-
124. p-Ethoxyphenyl 4'-(trans-4-butylcyclohexyl)-2'-fluorobiphenyl-4-carboxylate.
125. Ethyl 2'-fluoro-4'-(trans-4-pentylcyclohexyl)-biphenyl-4-carboxylate, m.p. 53.5°, c.p. 153.4°.
126. Propyl 2'-fluoro-4'-(trans-4-pentylcyclohexyl)-biphenyl-4-carboxylate.
127. Butyl 2'-fluoro-4'-(trans-4-pentylcyclohexyl)-biphenyl-4-carboxylate, m.pl. 52°, c.p. 120.3°.
128. Pentyl 2'-fluoro-4'-(trans-4-pentylcyclohexyl)-biphenyl-4-carboxylate.
129. Hexyl 2'-fluoro-4'-(trans-4-pentylcyclohexyl)-biphenyl-4-carboxylate.
130. 1-Methylheptyl 2'-fluoro-4'-(trans-4-pentylcyclohexyl)-biphenyl-4-carboxylate.
131. Trans-4-propylcyclohexyl 2'-fluoro-4'-(trans-4-pentylcyclohexyl)-biphenyl-4-carboxylate.
132. Trans-4-pentylcyclohexyl 2'-fluoro-4'-(trans-4-pentylcyclohexyl)-biphenyl-4-carboxylate.
133. p-Propylphenyl 2'-fluoro-4'-(trans-4-pentylcyclohexyl)-biphenyl-4-carboxylate.
134. p-Pentylphenyl 2'-fluoro-4'-(trans-4-pentylcyclohexyl)-biphenyl-4-carboxylate.
135. p-Methoxyphenyl 2'-fluoro-4'-(trans-4-pentylcyclohexyl)-biphenyl-4-carboxylate.
136. p-Ethoxyphenyl 2'-fluoro-4'-(trans-4-pentylcyclohexyl)-biphenyl-4-carboxylate.

Examples of dielectrics containing at least one compound of Formula I follow:

EXAMPLE A

A mixture of 28% of p-(trans-4-pentylcyclohexyl)-benzonitrile, 11% of 2-p-cyanophenyl-5-pentyl-1,3-dioxane, 32% of 4-pentyl-4'-cyanobiphenyl, 9% of 4-(trans-4-pentylcyclohexyl)-4'-cyanobiphenyl and 20% of 4'-acetyl-2-fluoro-4-(trans-4-pentylcyclohexyl)-biphenyl has a m.p. of −11° and a c.p. of 80°.

EXAMPLE B

A mixture of 18% of p-(trans-4-propylcyclohexyl)-benzonitrile, 26% of p-(trans-4-pentylcyclohexyl)-benzonitrile, 13% p-ethoxyphenyl trans-4-propylcyclohexanecarboxylate, 12% of p-ethoxyphenyl trans-4-butyl-cyclohexanecarboxylate, 14% of p-methoxyphenyl trans-4-pentylcyclohexanecarboxylate and 17% of 4'-acetyl-2-fluoro-4-(trans-4-pentylcyclohexyl)-biphenyl has a m.p. of −14° and a c.p. of 77°.

EXAMPLE C

A mixture of 13% of p-(trans-4-ethylcyclohexyl)-benzonitrile, 18% of p-(trans-4-propylcyclohexyl)-benzonitrile, 13% of p-(trans-4-butylcyclohexyl)-benzonitrile, 25% of p-(trans-4-pentylcyclohexyl)-benzonitrile, 15% of p-(trans-4-heptylcyclohexyl)-benzonitrile and 16% of 4'-acetyl-2-fluoro-4-(trans-4-pentylcyclohexyl)-biphenyl has a m.p. of −17° and c.p. of 58°.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A halogenobiphenyl derivative of the formula

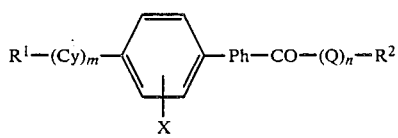

wherein $R^1$ and $R^2$ are each alkyl or alkoxy each of 1–10 C atoms; Cy is 1,4-cyclohexylene; Ph is 1,4-phenylene; Q is —O—Cy— or —O—Ph; m and n are each 0 or 1; and X is F, Cl or Br, with the proviso that when $R^1$ is alkoxy, $R^2$ is alkyl and m and n are both 0, then X is not Br; and when $R^1$ and $R^2$ are both alkoxy and m and n are both 0, then X is not F or Cl.

2. 4'-Acetyl-2-fluoro-4-(4-trans-n-pentylcyclohexyl)-biphenyl a compound of claim 1.

3. A compound of claim 1 wherein $R^1$ and $R^2$ are straight chained.

4. A compound of claim 1 wherein $R^1$ and $R^2$ are alkyl.

5. A compound of claim 1 wherein $R^1$ and $R^2$ are of 1–6 C atoms.

6. A compound of claim 1 of the formula $R^1$—Cy—Phx—Ph—CO—$R^3$ $R^1$—Phx—Ph—COOR$^3$ wherein $R^3$ is $C_{1-10}$-alkyl and Phx is 1,4-phenylene substituted by X.

7. A compound of claim 1 of the formula
$R^1$—Phx—Ph—CO—$R^3$
$R^1$—Phx—Ph—CO—O—Cy—$R^2$
$R^1$—Phx—Ph—CO—O—Ph—$R^2$
$R^1$—Cy—Phx—Ph—COOR$^3$
$R^1$—Cy—Phx—Ph—CO—O—Cy—$R^2$
$R^1$—Cy—Phx—Ph—CO—O—Ph—$R^2$ wherein $R^3$ is $C_{1-10}$-alkyl and Phx is 1,4-phenylene substituted by X.

8. A compound of claim 1 wherein one of $R^1$ and $R^2$ is branched and contains only 1 chain branching.

9. A compound of claim 1 wherein all cyclohexylene radicals contain both substituents in the trans position.

10. A compound of claim 1 wherein X is in the 2' position with respect to the adjacent unsubstituted 1,4-phenylene group.

11. A compound of claim 1 wherein one or both of m and n are 1.

12. A compound of claim 1 wherein m=n=0 and $R^1$ is alkyl.

13. A compound of claim 1 of the formula:

$R^1$—Cy—Phx—Ph—CO—$R^3$ wherein $R^3$ is $C_{1-10}$-alkyl and Phx is 1,4-phenylene substituted by x.

14. A compound of claim 1 of the formula:

$R^1$—Cy—Phx—Ph—COOR$^3$ wherein $R^3$ is $C_{1-10}$-alkyl and Phx is 1,4-phenylene substituted by x.

* * * * *